US009637428B2

(12) United States Patent
Hudson et al.

(10) Patent No.: US 9,637,428 B2
(45) Date of Patent: May 2, 2017

(54) HYDROCARBON GAS PROCESSING

(71) Applicants: Ortloff Engineers, Ltd., Midland, TX (US); S.M.E. Products, LP, Houston, TX (US)

(72) Inventors: Hank M. Hudson, Midland, TX (US); John D. Wilkinson, Midland, TX (US); Joe T. Lynch, Midland, TX (US); Scott A. Miller, Midland, TX (US); Kyle T. Cuellar, Katy, TX (US); Andrew F. Johnke, Beresford, SD (US); W. Larry Lewis, Houston, TX (US)

(73) Assignees: Ortloff Engineers, Ltd., Midland, TX (US); S.M.E. Products, LP, Houston, TX (US)

( * ) Notice: Subject to any disclaimer, the term of this patent is extended or adjusted under 35 U.S.C. 154(b) by 297 days.

(21) Appl. No.: 14/462,056

(22) Filed: Aug. 18, 2014

(65) Prior Publication Data
US 2015/0073194 A1 Mar. 12, 2015
US 2015/0315104 A2 Nov. 5, 2015

Related U.S. Application Data

(60) Provisional application No. 61/876,404, filed on Sep. 11, 2013.

(51) Int. Cl.
C07C 7/04 (2006.01)
F25J 1/00 (2006.01)
F25J 3/02 (2006.01)

(52) U.S. Cl.
CPC ............... C07C 7/04 (2013.01); F25J 1/0022 (2013.01); F25J 3/0209 (2013.01); F25J 3/0233 (2013.01);
(Continued)

(58) Field of Classification Search
None
See application file for complete search history.

(56) References Cited

U.S. PATENT DOCUMENTS 33,408 A 10/1861 Turner et al.
311,402 A 1/1885 Withington
(Continued)

OTHER PUBLICATIONS

Huebel, R., et al., "New NGL-Recovery Process Provides Viable Alternative", Oil & Gas Journal, Jan. 9, 2012 (9 pages).
(Continued)

Primary Examiner — Tam M Nguyen
(74) Attorney, Agent, or Firm — Fitzpatrick, Cella, Harper & Scinto

(57) ABSTRACT

A process and an apparatus are disclosed for a compact processing assembly to improve the recovery of $C_2$ (or $C_3$) and heavier hydrocarbon components from a hydrocarbon gas stream. The preferred method of separating a hydrocarbon gas stream generally includes producing at least a substantially condensed first stream and a cooled second stream, expanding both streams to lower pressure, and supplying the streams to a fractionation tower. In the process and apparatus disclosed, the expanded first stream is heated to form a vapor fraction and a liquid fraction. The vapor fraction is combined with the tower overhead vapor, directed to a heat and mass transfer means inside a processing assembly, and cooled and partially condensed by the expanded first stream to form a residual vapor stream and a condensed stream. The condensed stream is combined with the liquid fraction and supplied to the tower at its top feed point.

5 Claims, 8 Drawing Sheets

Figure 1:
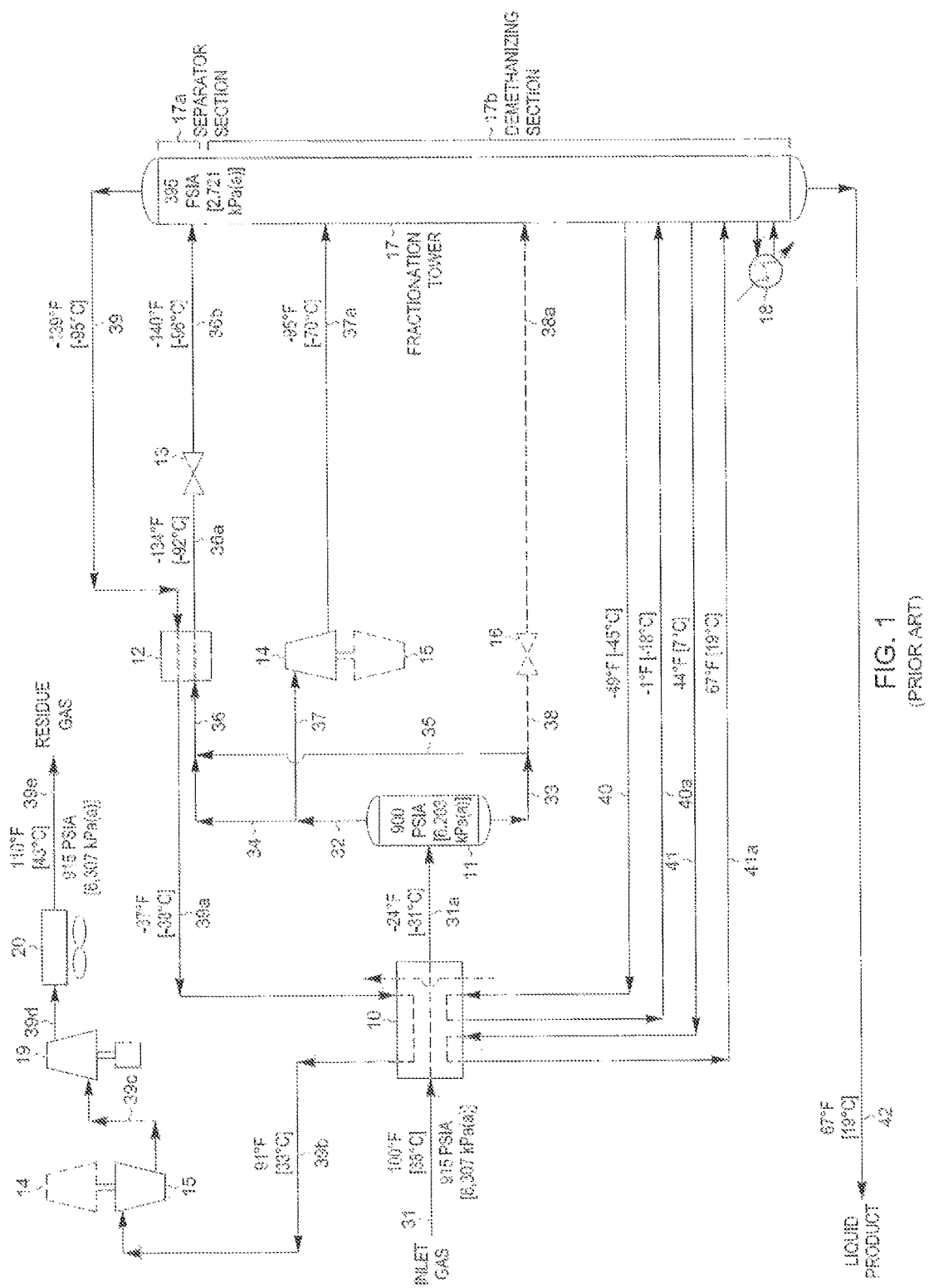

(52) U.S. Cl.
CPC ............ *F25J 3/0238* (2013.01); *F25J 3/0242* (2013.01); *F25J 2200/02* (2013.01); *F25J 2200/70* (2013.01); *F25J 2200/74* (2013.01); *F25J 2200/80* (2013.01); *F25J 2205/04* (2013.01); *F25J 2235/60* (2013.01); *F25J 2270/90* (2013.01); *F25J 2290/40* (2013.01)

(56) References Cited

U.S. PATENT DOCUMENTS

| | | |
|---|---|---|
| 3,292,380 A | 12/1966 | Bucklin |
| 3,292,980 A | 12/1966 | Gustafsson et al. |
| 3,477,915 A | 11/1969 | Gantt et al. |
| 3,508,412 A | 4/1970 | Yearout |
| 3,516,261 A | 6/1970 | Hoffman |
| 3,625,017 A | 12/1971 | Hoffman |
| 3,797,261 A | 3/1974 | Juncker et al. |
| 3,983,711 A | 10/1976 | Solomon |
| 4,061,481 A | 12/1977 | Campbell et al. |
| 4,127,009 A | 11/1978 | Phillips |
| 4,140,504 A | 2/1979 | Campbell et al. |
| 4,157,904 A | 6/1979 | Campbell et al. |
| 4,171,964 A | 10/1979 | Campbell et al. |
| 4,185,978 A | 1/1980 | McGalliard et al. |
| 4,251,249 A | 2/1981 | Gulsby |
| 4,278,457 A | 7/1981 | Campbell et al. |
| 4,519,824 A | 5/1985 | Huebel |
| 4,617,039 A | 10/1986 | Buck |
| 4,687,499 A | 8/1987 | Aghili |
| 4,688,399 A | 8/1987 | Reimann |
| 4,689,063 A | 8/1987 | Paradowski et al. |
| 4,690,702 A | 9/1987 | Paradowski et al. |
| 4,854,955 A | 8/1989 | Campbell et al. |
| 4,869,740 A | 9/1989 | Campbell et al. |
| 4,889,545 A | 12/1989 | Campbell et al. |
| 5,255,528 A | 10/1993 | Dao |
| 5,275,005 A | 1/1994 | Campbell et al. |
| 5,282,507 A | 2/1994 | Tongu et al. |
| 5,316,628 A | 5/1994 | Collin et al. |
| 5,335,504 A | 8/1994 | Durr et al. |
| 5,339,654 A | 8/1994 | Cook et al. |
| 5,367,884 A | 11/1994 | Phillips et al. |
| 5,410,885 A | 5/1995 | Smolarek et al. |
| 5,555,748 A | 9/1996 | Campbell et al. |
| 5,566,554 A | 10/1996 | Vijayaraghavan et al. |
| 5,568,737 A | 10/1996 | Campbell et al. |
| 5,675,054 A | 10/1997 | Manley et al. |
| 5,685,170 A | 11/1997 | Sorensen |
| 5,713,216 A | 2/1998 | Erickson |
| 5,771,712 A | 6/1998 | Campbell et al. |
| 5,799,507 A | 9/1998 | Wilkinson et al. |
| 5,881,569 A | 3/1999 | Campbell et al. |
| 5,890,377 A | 4/1999 | Foglietta |
| 5,890,378 A | 4/1999 | Rambo et al. |
| 5,942,164 A | 8/1999 | Tran |
| 5,983,664 A | 11/1999 | Campbell et al. |
| 6,077,985 A | 6/2000 | Stork |
| 6,182,469 B1 | 2/2001 | Campbell et al. |
| 6,361,582 B1 | 3/2002 | Pinnau et al. |
| 6,516,631 B1 | 2/2003 | Trebble |
| 6,565,626 B1 | 5/2003 | Baker et al. |
| 6,578,379 B2 | 6/2003 | Paradowski |
| 6,694,775 B1 | 2/2004 | Higginbotham et al. |
| 6,712,880 B2 | 3/2004 | Foglietta et al. |
| 6,742,358 B2 | 6/2004 | Wilkinson et al. |
| 6,915,662 B2 | 7/2005 | Wilkinson et al. |
| 7,010,937 B2 | 3/2006 | Wilkinson et al. |
| 7,165,423 B2 | 1/2007 | Winningham |
| 7,191,617 B2 | 3/2007 | Cuellar et al. |
| 7,204,100 B2 | 4/2007 | Wilkinson et al. |
| 7,210,311 B2 | 5/2007 | Wilkinson |
| 7,219,513 B1 | 5/2007 | Mostafa |
| 7,565,815 B2 | 7/2009 | Wilkinson et al. |
| 7,631,516 B2 | 12/2009 | Cuellar et al. |
| 7,713,497 B2 | 5/2010 | Mak |
| 8,156,758 B2 | 4/2012 | Denton et al. |
| 8,434,325 B2 | 5/2013 | Martinez et al. |
| 8,590,340 B2 | 11/2013 | Pitman et al. |
| 8,881,549 B2 | 11/2014 | Johnke et al. |
| 8,919,148 B2 | 12/2014 | Wilkinson et al. |
| 9,021,831 B2 | 5/2015 | Johnke et al. |
| 9,021,832 B2 | 5/2015 | Pierce et al. |
| 9,052,136 B2 | 6/2015 | Johnke et al. |
| 9,052,137 B2 | 6/2015 | Johnke et al. |
| 9,057,558 B2 | 6/2015 | Johnke et al. |
| 9,068,774 B2 | 6/2015 | Johnke et al. |
| 9,074,814 B2 | 7/2015 | Johnke et al. |
| 9,080,810 B2 | 7/2015 | Pitman et al. |
| 9,080,811 B2 | 7/2015 | Johnke et al. |
| 2001/0008073 A1 | 7/2001 | Finn et al. |
| 2002/0166336 A1 | 11/2002 | Wilkinson et al. |
| 2004/0079107 A1 | 4/2004 | Wilkinson et al. |
| 2004/0172967 A1 | 9/2004 | Patel et al. |
| 2005/0229634 A1 | 10/2005 | Huebel et al. |
| 2005/0247078 A1 | 11/2005 | Wilkinson et al. |
| 2005/0268649 A1 | 12/2005 | Wilkinson et al. |
| 2006/0032269 A1 | 2/2006 | Cuellar et al. |
| 2006/0086139 A1 | 4/2006 | Eaton et al. |
| 2006/0283207 A1 | 12/2006 | Pitman et al. |
| 2008/0000265 A1 | 1/2008 | Cuellar et al. |
| 2008/0078205 A1 | 4/2008 | Cuellar et al. |
| 2008/0190136 A1 | 8/2008 | Pitman et al. |
| 2008/0271480 A1 | 11/2008 | Mak |
| 2009/0107175 A1 | 4/2009 | Patel et al. |
| 2009/0293538 A1 | 12/2009 | Wilkinson et al. |
| 2010/0251764 A1 | 10/2010 | Johnke et al. |
| 2010/0275647 A1 | 11/2010 | Johnke et al. |
| 2010/0287983 A1 | 11/2010 | Johnke et al. |
| 2010/0287984 A1 | 11/2010 | Johnke et al. |
| 2010/0326134 A1 | 12/2010 | Johnke et al. |
| 2011/0067441 A1 | 3/2011 | Martinez et al. |
| 2011/0067442 A1 | 3/2011 | Martinez et al. |
| 2011/0067443 A1 | 3/2011 | Martinez et al. |
| 2011/0226011 A1 | 9/2011 | Johnke et al. |
| 2011/0226013 A1 | 9/2011 | Johnke et al. |
| 2011/0232328 A1 | 9/2011 | Johnke et al. |
| 2015/0073195 A1 | 3/2015 | Lynch et al. |
| 2015/0073196 A1 | 3/2015 | Miller et al. |

OTHER PUBLICATIONS

Supplemental Notice of Allowability issued in U.S. Appl. No. 12/689,616, dated Feb. 10, 2015 (12 pages).

Comments on Statement of Reasons for Allowance filed in U.S. Appl. No. 12/689,616, dated Mar. 3, 2015 (7 pages).

Response and Statement of Interview filed in U.S. Appl. No 13/052,575, dated Mar. 16, 2015 (37 pages).

Response and Statement of Interview filed in U.S. Appl. No. 13/052,348, dated Mar. 17, 2015 (37 pages).

Response and Statement of Interview filed in U.S. Appl. No. 13/053,792, dated Mar. 18, 2015 (37 pages).

Response, Statement of Interview and Petition for Extension of Time filed in U.S. Appl. No. 13/051,682, dated Mar. 19, 2015 (37 pages.).

Response, Statement of Interview and Petition for Extension of Time filed in U.S. Appl. No. 13/048,315, dated Mar. 20, 2015 (93 pages).

Amendment and Statement of Interview filed in U.S. Appl. No. 13/052,348, dated Mar. 26, 2015 (23 pages).

Amendment and Statement of Interview filed in U.S. Appl. No. 13/051,682, dated Mar. 26, 2015 (29 pages).

Amendment and Statement of Interview filed in U.S. Appl. No. 13/053,792, dated Mar. 26, 2015 (25 pages).

Amendment and Statement of Interview filed in U.S. Appl. No. 13/052,575, dated Mar. 26, 2015 (20 pages).

Notice of Allowance and Fee(s) Due issued in U.S. Appl. No. 12/689,616, dated Jan. 9, 2015 (15 pages).

Comments on Statement of Reasons for Allowance filed in U.S. Appl. No. 12/689,616, dated Jan. 30, 2015 (8 pages).

Office Action issued in U.S. Appl. No. 13/052,348, dated Dec. 17, 2014 (13 pages).

(56) References Cited

OTHER PUBLICATIONS

Office Action issued in U.S. Appl. No. 13/051,682, dated Dec. 18, 2014 (13 pages).
Office Action issued in U.S. Appl. No. 13/053,792, dated Dec. 18, 2014 (20 pages).
Office Action issued in U.S. Appl. No. 13/052,575, dated Dec. 16, 2014 (16 pages).
Advisory Action Before the Filing of an Appeal Brief issued in U.S. Appl. No. 12/689,616, dated Nov. 28, 2014 (3 pages).
Submission Under 37 C.F.R. § 1.114, Statement of Interview, and Petition for Extension of Time filed in U.S. Appl. No. 12/689,616, dated Dec. 8, 2014 (39 pages).
International Search Report and Written Opinion issued in International Application No. PCT/US2011/028872 dated May 18, 2011—7 pages.
International Search Report and Written Opinion issued in International Application No. PCT/US2011/29234 dated May 20, 2011—30 pages.
International Search Report and Written Opinion issued in International Application No. PCT/US2011/029034 dated Jul. 27, 2011—40 pages.
International Search Report and Written Opinion issued in International Application No. PCT/US2011/029409 dated May 17, 2011—15 pages.
International Search Report and Written Opinion issued in International Application No. PCT/US2011/029239 dated May 20, 2011—21 pages.
E. Ross Mowrey, "Efficient, High Recovery of Liquids From Natural Gas Utilizing a High Pressure Absorber," Proceedings of the Eighty-First Annual Convention of the Gas Processors Association, Dallas, Texas, Mar. 11-13, 2002.
"Dew Point Control Gas Conditioning Units," SME Products Brochure, Gas Processors Assoc. Conference (Apr. 5, 2009).
"Fuel Gas Conditioning Units for Compressor Engines," SME Products Brochure, Gas Processors Assoc. Conference (Apr. 5, 2009).
"P&ID Fuel Gas Conditioner," Drawing No. SMEP-901, Date Drawn: Aug. 29, 2007, SME, available at http://www.sme-llc.com/sme.cfm?a=prd&catID=58&subID=44&prdID=155 (Apr. 24, 2009).
"Fuel Gas Conditioner Preliminary Arrangement," Drawing No. SMP-1007-00, Date Drawn: Nov. 11, 2008, SME, available at http://www.sme-llc.com/sme.cfm?a=prd&catID=58&subID=44&prdID=155 (Apr. 24, 2009).
"Product: Fuel Gas Conditioning Units," SME Associates, LLC, available at http://www.smellc.com/sme.cfm?a=prd&catID=58&subID=44&prdID=155 (Apr. 24, 2009).
International Search Report and Written Opinion issued in International Application No. PCT/US2010/21364 dated Mar. 29, 2010—20 pages.
International Search Report and Written Opinion issued in International Application No. PCT/US2010/26185 dated Jul. 9, 2010—20 pages.
International Search Report and Written Opinion issued in corresponding International Application No. PCT/US2010/29331 dated Jul. 2, 2010—15 pages.
International Search Report and Written Opinion issued in International Application No. PCT/US2010/33374 dated Jul. 9, 2010—18 pages.
International Search Report and Written Opinion issued in International Application No. PCT/US2010/35121 dated Jul. 19, 2010—18 pages.
International Search Report and Written Opinion issued in International Application No. PCT/US2010/37098 dated Aug. 17, 2010—12 pages.
International Search Report and Written Opinion issued in International Application No, PCT/US14/51544 dated Nov. 24, 2014—16 pages.

HYDROCARBON GAS PROCESSING

BACKGROUND OF THE INVENTION

This invention relates to a process and apparatus for improving the separation of a gas containing hydrocarbons. The applicants claim the benefits under Title 35, United States Code, Section 119(e) of prior U.S. Provisional Application No. 61/876,404 which was filed on Sep. 11, 2013. Assignees S.M.E. Products LP and Ortloff Engineers, Ltd. were parties to a joint research agreement that was in effect before the invention of this application was made.

Ethylene, ethane, propylene, propane, and/or heavier hydrocarbons can be recovered from a variety of gases, such as natural gas, refinery gas, and synthetic gas streams obtained from other hydrocarbon materials such as coal, crude oil, naphtha, oil shale, tar sands, and lignite. Natural gas usually has a major proportion of methane and ethane, i.e., methane and ethane together comprise at least 50 mole percent of the gas. The gas also contains relatively lesser amounts of heavier hydrocarbons such as propane, butanes, pentanes, and the like, as well as hydrogen, nitrogen, carbon dioxide, and/or other gases.

The present invention is generally concerned with improving the recovery of ethylene, ethane, propylene, propane, and heavier hydrocarbons from such gas streams. A typical analysis of a gas stream to be processed in accordance with this invention would be, in approximate mole percent, 90.3% methane, 4.0% ethane and other $C_2$ components, 1.7% propane and other $C_3$ components, 0.3% iso-butane, 0.5% normal butane, and 0.8% pentanes plus, with the balance made up of nitrogen and carbon dioxide. Sulfur containing gases are also sometimes present.

The historically cyclic fluctuations in the prices of both natural gas and its natural gas liquid (NGL) constituents have at times reduced the incremented value of ethane, ethylene, propane, propylene, and heavier components as liquid products. This has resulted in a demand for processes that can provide more efficient recoveries of these products, for processes that can provide efficient recoveries with lower capital investment, and for processes that can be easily adapted or adjusted to vary the recovery of a specific component over a broad range. Available processes for separating these materials include those based upon cooling and refrigeration of gas, oil absorption, and refrigerated oil absorption. Additionally, cryogenic processes have become popular because of the availability of economical equipment that produces power while simultaneously expanding and extracting heat from the gas being processed. Depending upon the pressure of the gas source, the richness (ethane, ethylene, and heavier hydrocarbons content) of the gas, and the desired end products, each of these processes or a combination thereof may be employed.

The cryogenic expansion process is now generally preferred for natural gas liquids recovery because it provides maximum simplicity with ease of startup, operating flexibility, good efficiency, safety, and good reliability. U.S. Pat. Nos. 3,292,380; 4,061,481; 4,140,504; 4,157,904; 4,171,964; 4,185,978; 4,251,249; 4,278,457; 4,519,824; 4,617,039; 4,687,499; 4,689,063; 4,690,702; 4,854,955; 4,869,740; 4,889,545; 5,275,005; 5,555,748; 5,566,554; 5,568,737; 5,771,712; 5,799,507; 5,881,569; 5,890,378; 5,983,664; 6,182,469; 6,578,379; 6,712,880; 6,915,662; 7,191,617; 7,219,513; 8,590,340; reissue U.S. Pat. No. 33,408; and co-pending application Nos. 11/430,412; 11/839,693; 12/206,230; 12/689,616; 12/717,394; 12/750,862; 12/772,472; 12/781,259; 12/868,993; 12/869,007; 12/869,139; 12/979,563; 13/048,315; 13/051,682; 13/052,348; 13/052,575; and 13/053,792 describe relevant processes (although the description of the present invention in some cases is based on different processing conditions than those described in the cited U.S. Patents and co-pending applications).

In a typical cryogenic expansion recovery process, a feed gas stream under pressure is cooled by heat exchange with other streams of the process and/or external sources of refrigeration such as a propane compression-refrigeration system. As the gas is cooled, liquids may be condensed and collected in one or more separators as high-pressure liquids containing some of the desired $C_2$+ components. Depending on the richness of the gas and the amount of liquids formed, the high-pressure liquids may be expanded to a lower pressure and fractionated. The vaporization occurring during expansion of the liquids results in further cooling of the stream. Under some conditions, pre-cooling the high pressure liquids prior to the expansion may be desirable in order to further lower the temperature resulting from the expansion. The expanded stream, comprising a mixture of liquid and vapor, is fractionated in a distillation (demethanizer or deethanizer) column. In the column, the expansion cooled stream(s) is (are) distilled to separate residual methane, nitrogen, and other volatile gases as overhead vapor from the desired $C_2$ components, $C_3$ components, and heavier hydrocarbon components as bottom liquid product, or to separate residual methane, $C_2$ components, nitrogen, and other volatile gases as overhead vapor from the desired $C_3$ components and heavier hydrocarbon components as bottom liquid product.

If the feed gas is not totally condensed (typically it is not), the vapor remaining from the partial condensation can be split into two streams. One portion of the vapor is passed through a work expansion machine or engine, or an expansion valve, to a lower pressure at which additional liquids are condensed as a result of further cooling of the stream. The pressure after expansion is essentially the same as the pressure at which the distillation column is operated. The combined vapor-liquid phases resulting from the expansion are supplied as feed to the column.

The remaining portion of the vapor is cooled to substantial condensation by heat exchange with other process streams, e.g., the cold fractionation tower overhead. Some or all of the high-pressure liquid may be combined with this vapor portion prior to cooling. The resulting cooled stream is then expanded through an appropriate expansion device, such as an expansion valve, to the pressure at which the demethanizer is operated. During expansion, a portion of the liquid will vaporize, resulting in cooling of the total stream. The flash expanded stream is then supplied as top feed to the demethanizer. Typically, the vapor portion of the flash expanded stream and the demethanizer overhead vapor combine in an upper separator section in the fractionation tower as residual methane product gas. Alternatively, the cooled and expanded stream may be supplied to a separator to provide vapor and liquid streams. The vapor is combined with the tower overhead and the liquid is supplied to the column as a top column feed.

In the ideal operation of such a separation process, the residue gas leaving the process will contain substantially all of the methane in the feed gas with essentially none of the heavier hydrocarbon components, and the bottoms fraction leaving the demethanizer will contain substantially all of the heavier hydrocarbon components with essentially no methane or more volatile components. In practice, however, this ideal situation is not obtained because the conventional demethanizer is operated largely as a stripping column. The methane product of the process, therefore, typically comprises vapors leaving the top fractionation stage of the column, together with vapors not subjected to any rectification step. Considerable losses of $C_2$, $C_3$, and $C_4+$ components occur because the top liquid feed contains substantial quantities of these components and heavier hydrocarbon components, resulting in corresponding equilibrium quantities of $C_2$ components, $C_3$ components, $C_4$ components, and heavier hydrocarbon components in the vapors leaving the top fractionation stage of the demethanizer. The loss of these desirable components could be significantly reduced if the rising vapors could be brought into contact with a significant quantity of liquid (reflux) capable of absorbing the $C_2$ components, $C_3$ components, $C_4$ components, and heavier hydrocarbon components from the vapors.

In recent years, the preferred processes for hydrocarbon separation use an upper absorber section to provide additional rectification of the rising vapors. For many of these processes, the source of the reflux stream for the upper rectification section is a recycled stream of residue gas supplied under pressure. The recycled residue gas stream is usually cooled to substantial condensation by heat exchange with other process streams, e.g., the cold fractionation tower overhead. The resulting substantially condensed stream is then expanded through an appropriate expansion device, such as an expansion valve, to the pressure at which the demethanizer is operated. During expansion, a portion of the liquid will usually vaporize, resulting in cooling of the total stream. The flash expanded stream is then supplied as top feed to the demethanizer. Typical process schemes of this type are disclosed in U.S. Pat. Nos. 4,889,545; 5,568,737; and 5,881,569, in co-pending application Ser. Nos. 12/717, 394 and 13/052,348, and in Mowrey, E. Ross, "Efficient, High Recovery of Liquids from Natural Gas Utilizing a High Pressure Absorber", Proceedings of the Eighty-First Annual Convention of the Gas Processors Association, Dallas, Tex. Mar. 11-13, 2002. Unfortunately, in addition to the additional rectification section in the demethanizer, these processes also require the use of a compressor to provide the motive force for recycling the reflux stream to the demethanizer, adding to both the capital cost and the operating cost of facilities using these processes.

Another method of generating a reflux stream for the upper rectification section is to use the flash expanded substantially condensed stream to cool and partially condense the column overhead vapor, with the heated flash expanded stream then directed to a mid-column feed point on the demethanizer. The liquid condensed from the column overhead vapor is separated and supplied as top feed to the demethanizer, while the uncondensed vapor is discharged as the residual methane product gas. The heated flash expanded stream is only partially vaporized, and so contains a substantial quantity of liquid that serves as supplemental reflux for the demethanizer, so that the top reflux feed can then rectify the vapors leaving the lower section of the column. U.S. Pat. No. 4,854,955 is an example of this type of process. Unfortunately, this type of process requires the additional rectification section plus the reflux condenser, drum, and pumps to generate the reflux stream for the column, adding to the capital cost of facilities using this process.

However, there are many gas processing plants that have been built in the U.S. and other countries according to U.S. Pat. Nos. 4,157,904 and 4,278,457 (as well as other processes) that have no upper absorber section to provide additional rectification of the rising vapors and cannot be easily modified to add this feature. Also, these plants do not usually have surplus compression capacity to allow recycling a reflux stream, nor do their demethanizer or deethanizer columns have surplus fractionation capacity to accommodate the increase in feed rate that results when a new reflux stream is added. As a result, these plants are not as efficient when operated to recover $C_2$ components and heavier components from the gas (commonly referred to as "ethane recovery"), and are particularly inefficient when operated to recover only the $C_3$ components and heavier components from the gas (commonly referred to as "ethane rejection").

The present invention is a novel means of providing additional rectification (similar to what is used in U.S. Pat. No. 4,854,955 and co-pending application Ser. Nos. 12/772, 472 and 13/053,792) that can be easily added to existing gas processing plants to increase the recovery of the desired $C_3$ components without requiring additional compression or fractionation capacity. The incremental value of this increased recovery is often substantial. For the Examples given later, the incremental income from the additional recovery capability over that of the prior art is in the range of US$ 575,000 to US$ 1,120,000 [€ 430,000 to € 835, 000] per year using an average incremental value US$ 0.74-1.08 per gallon [€ 145-214 per m$^3$] for hydrocarbon liquids compared to the corresponding hydrocarbon gases.

The present invention also combines what heretofore have been individual equipment items into a common housing, thereby reducing both the plot space requirements and the capital cost of the addition. Surprisingly, applicants have found that the more compact arrangement also significantly increases the product recovery at a given power consumption, thereby increasing the process efficiency and reducing the operating cost of the facility. In addition, the more compact arrangement also eliminates much of the piping used to interconnect the individual equipment items in traditional plant designs, further reducing capital cost and also eliminating the associated flanged piping connections. Since piping flanges are a potential leak source for hydrocarbons (which are volatile organic compounds, VOCs, that contribute to greenhouse gases and may also be precursors to atmospheric ozone formation), eliminating these flanges reduces the potential for atmospheric emissions that may damage the environment.

In accordance with the present invention, it has been found that $C_2$ recoveries in excess of 89% can be obtained. Similarly, in those instances where recovery of $C_2$ components is not desired, $C_3$ recoveries in excess of 99% can be maintained. The present invention, although applicable at lower pressures and warmer temperatures, is particularly advantageous when processing feed gases in the range of 400 to 1500 psia [2,758 to 10,342 kPa(a)] or higher under conditions requiring NGL recovery column overhead temperatures of $-50°$ F. [$-46°$ C] or colder.

Figure 2:
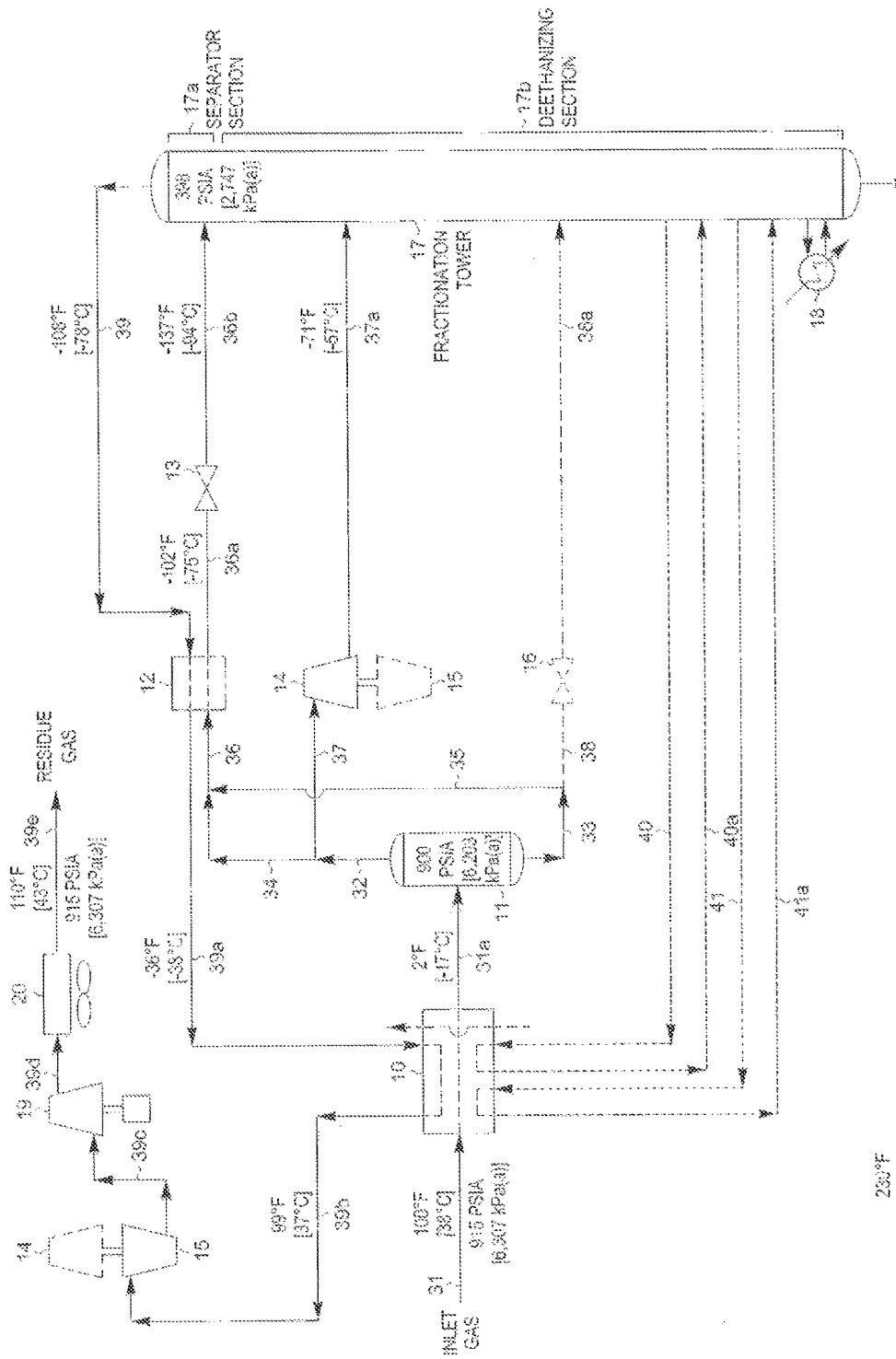
Figure 3:
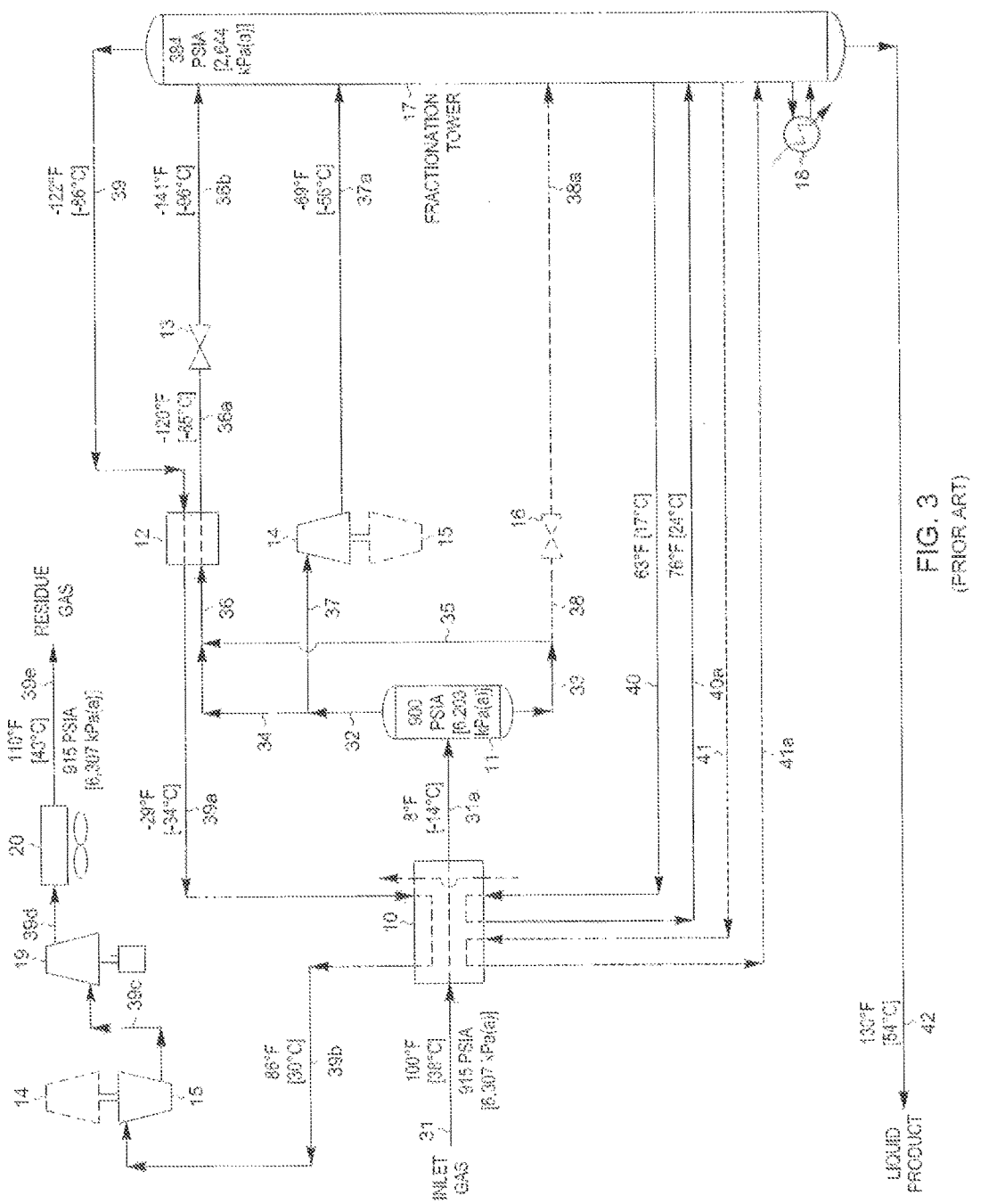
Figure 4:
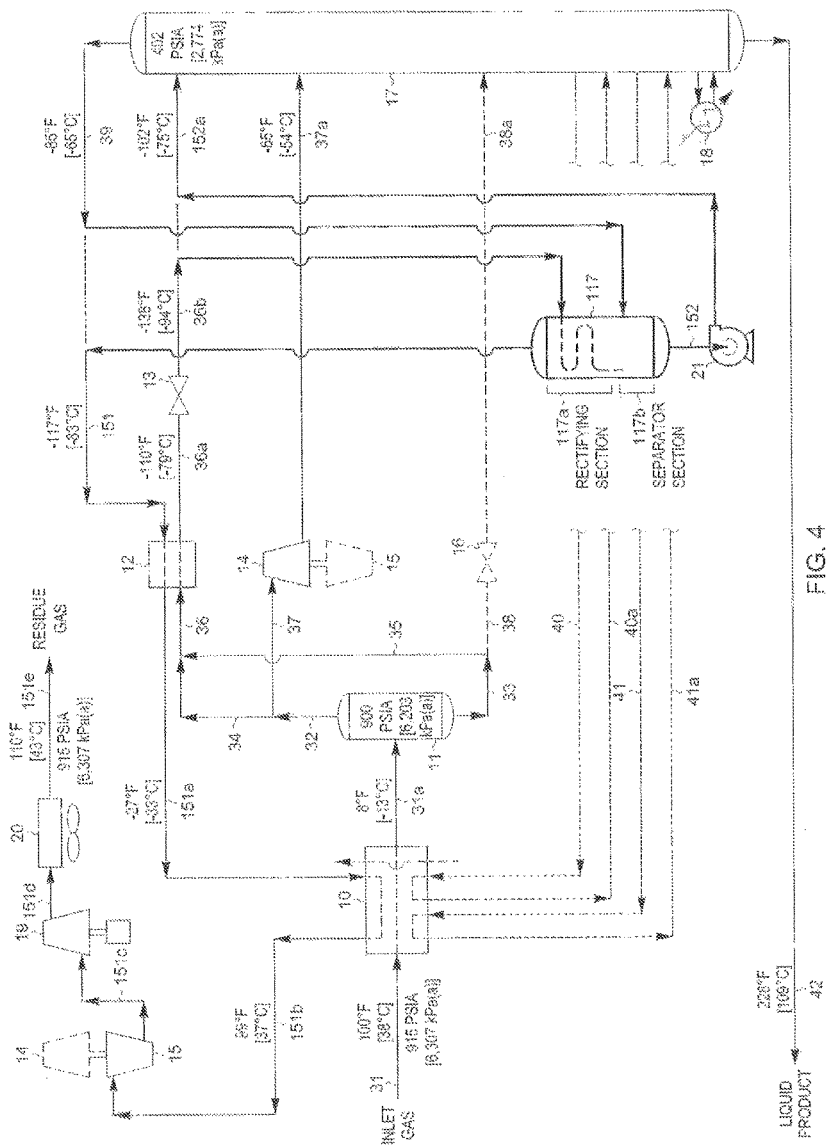
Figure 5:
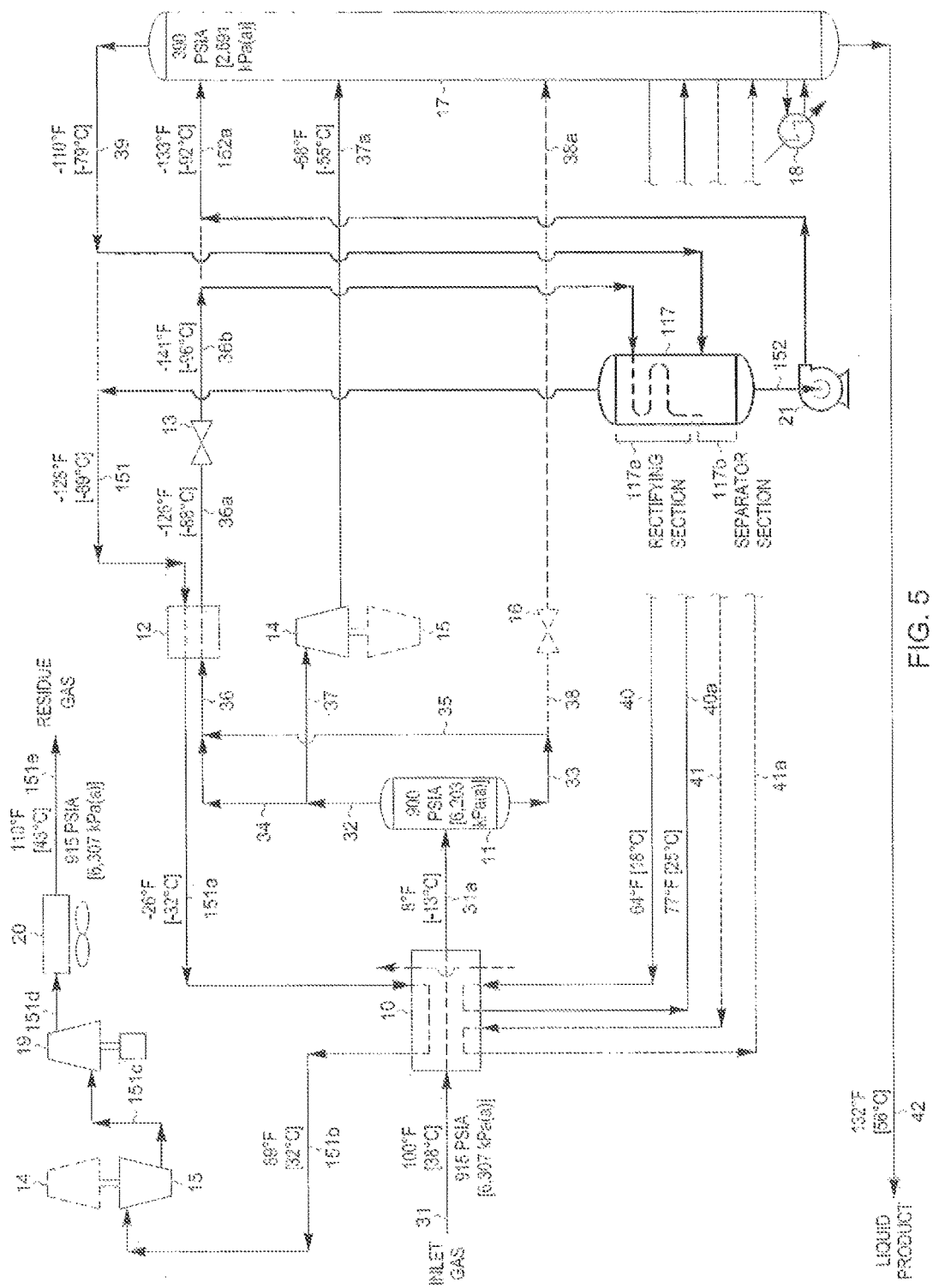
Figure 6:
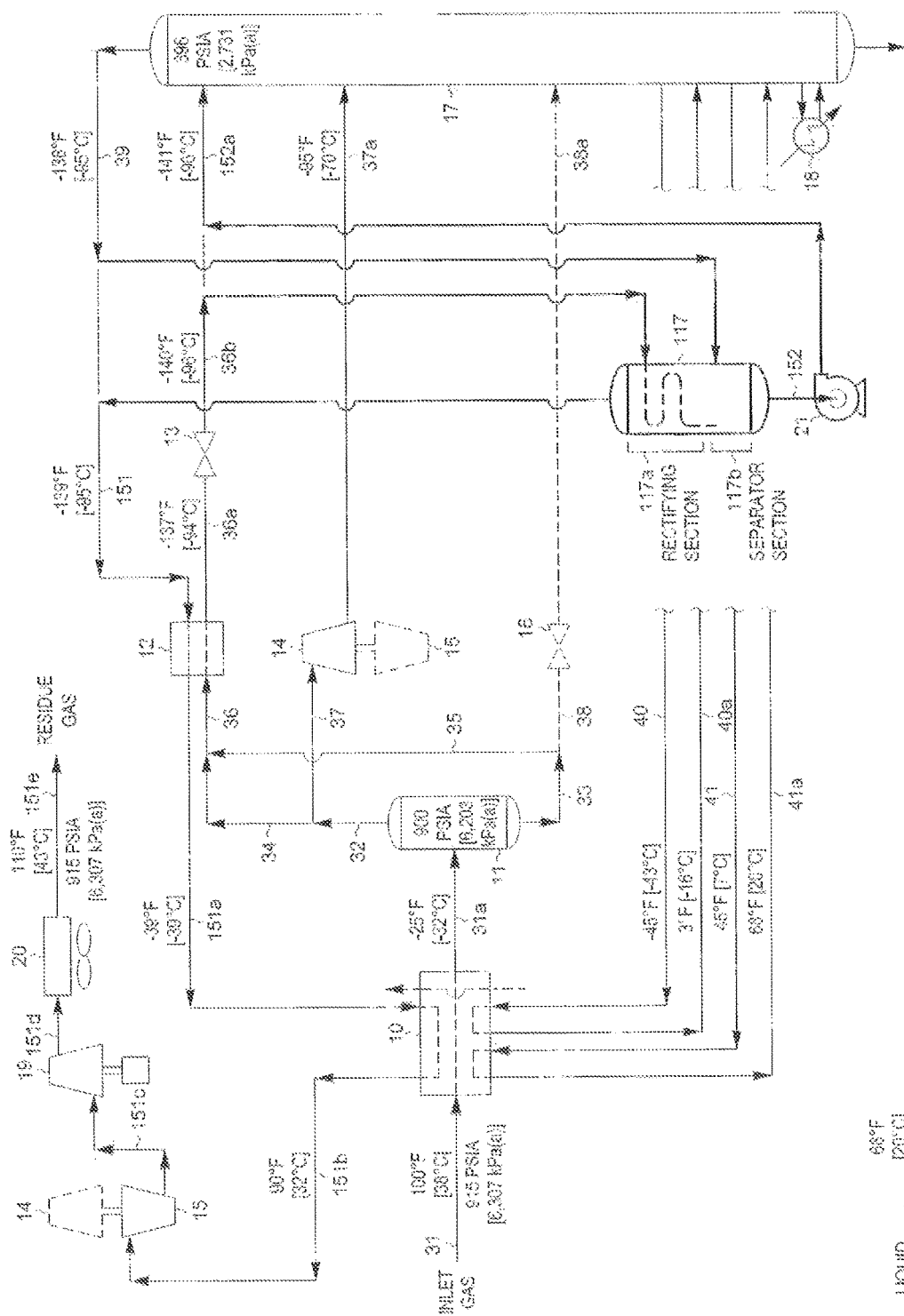
Figure 7:
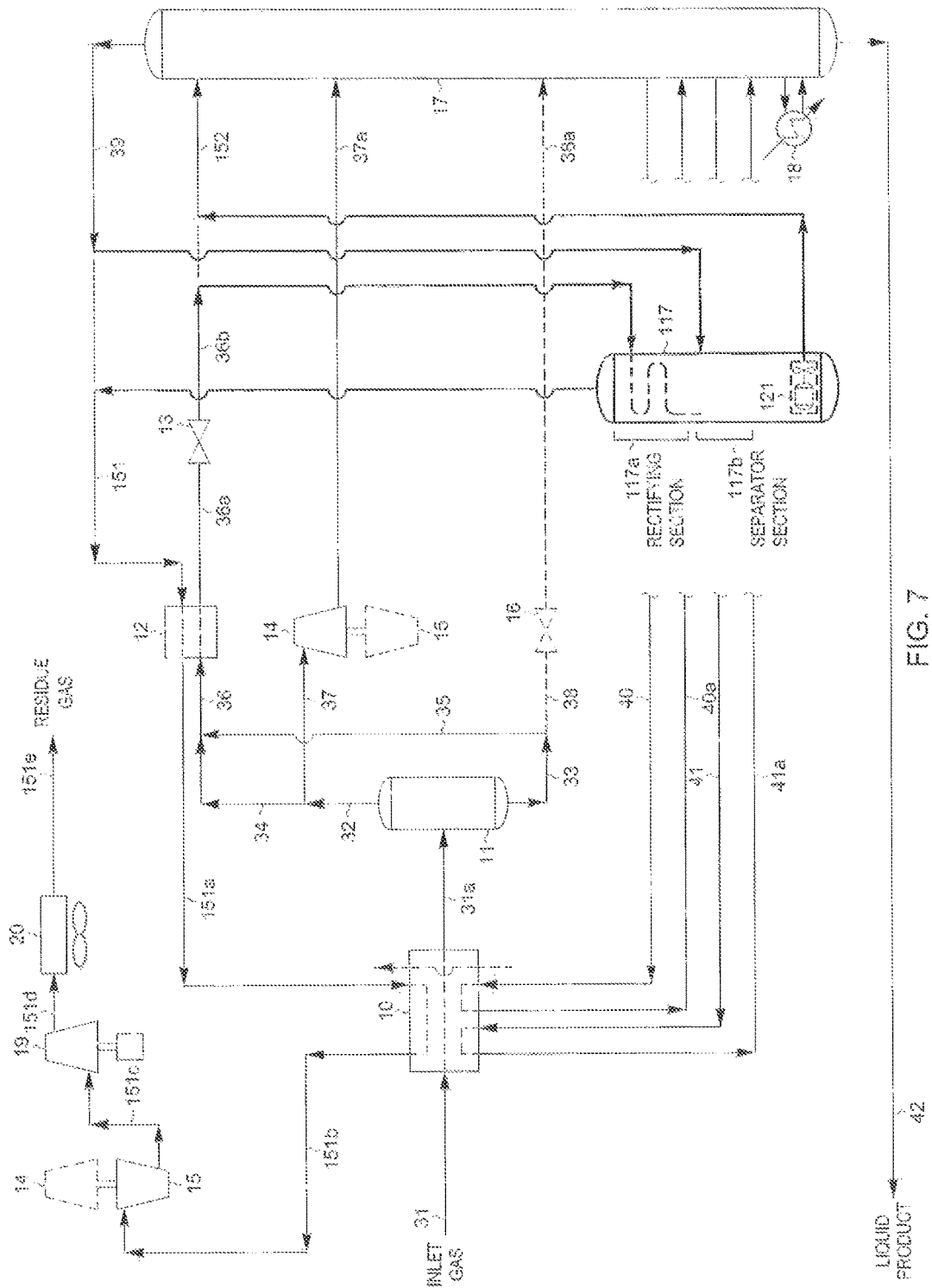
Figure 8:
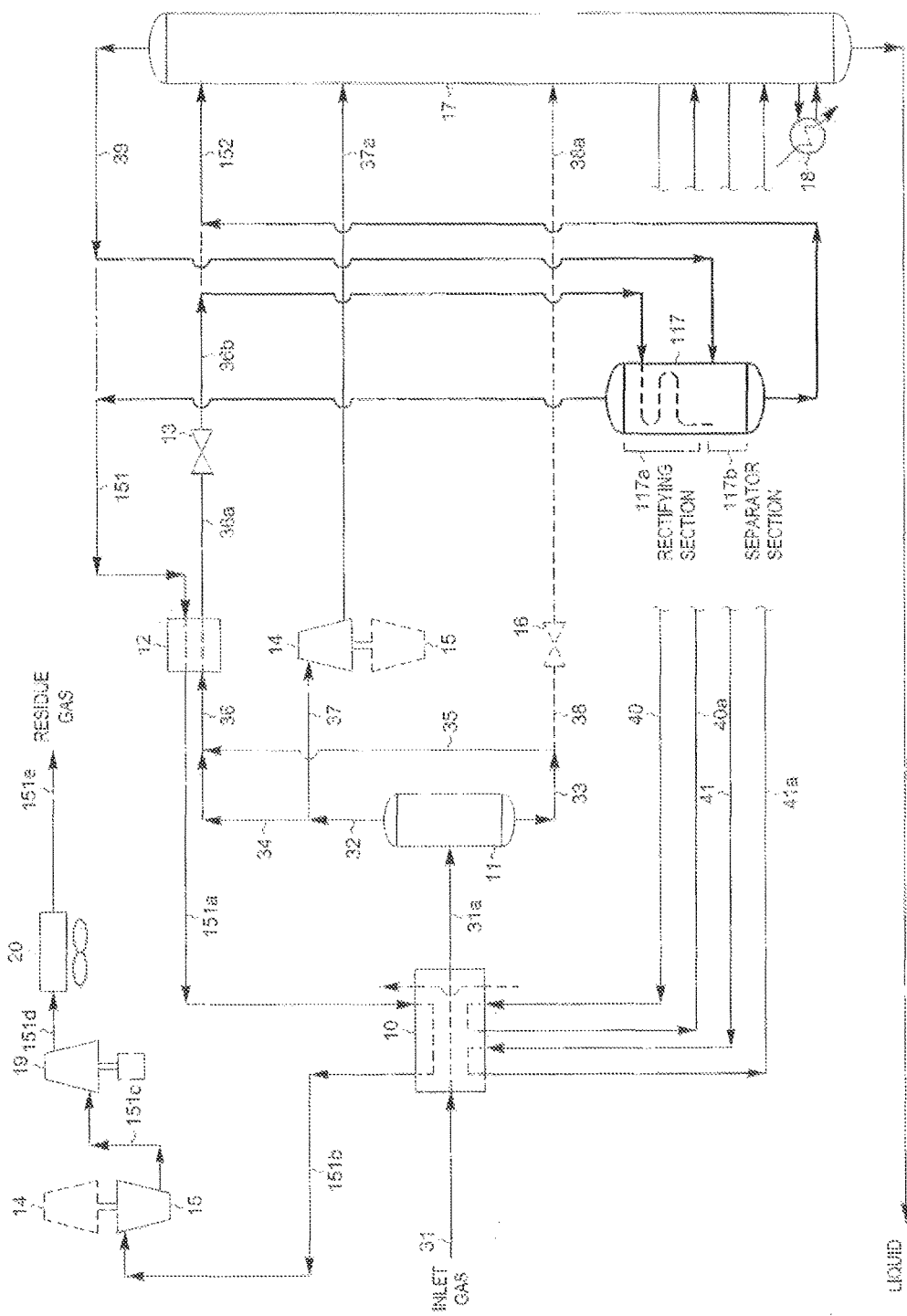

For a better understanding of the present invention, reference is made to the following examples and drawings. Referring to the drawings:

FIGS. 1, 2, and 3 are flow diagrams of prior art natural gas processing plants in accordance with U.S. Pat. No. 4,157, 904 or 4,278,457;

FIGS. 4, 5 and 6 are flow diagrams of natural gas processing plants adapted to use the present invention; and FIGS. 7 and 8 are flow diagrams illustrating alternative means of application of the present invention to a natural gas processing plant.

In the following explanation of the above figures, tables, are provided summarizing flow rates calculated for representative process conditions. In the tables appearing herein, the values for flow rates (in moles per hour) have been rounded to the nearest whole number for convenience. The total stream rates shown in the tables include all non-hydrocarbon components and hence are generally larger than the sum of the stream flow rates for the hydrocarbon components. Temperatures indicated are approximate values rounded to the nearest degree. It should also be noted that the process design calculations performed for the purpose of comparing the processes depicted in the figures are based on the assumption of no heat leak from (or to) the surroundings to (or from) the process. The quality of commercially available insulating materials makes this a very reasonable assumption and one that is typically made by those skilled in the art.

For convenience, process parameters are repeated in both the traditional British units and in the units of the Systéme International d'Unités (SI). The molar flow rates given in the tables may be interpreted as either pound moles per hour or kilogram moles per hour. The energy consumptions reported as horsepower (HP) and/or thousand British Thermal Units per hour (MBTU/Hr) correspond to the stated molar flow rates in pound moles per hour. The energy consumptions reported as kilowatts (kW) correspond to the stated molar flow rates in kilogram moles per hour.

DESCRIPTION OF THE PRIOR ART

FIG. 1 is a process flow diagram showing the design of a processing plant to recover $C_2$+ components from natural gas using prior art according to U.S. Pat. No. 4,157,904 or 4,278,457. In this simulation of the process, inlet gas enters the plant at 100° F. [38° C.] and 915 psia [6,307 kPa(a)] as stream 31. If the inlet gas contains a concentration of sulfur compounds which would prevent the product streams from meeting specifications, the sulfur compounds are removed by appropriate pretreatment of the feed gas (not illustrated). In addition, the feed stream is usually dehydrated to prevent hydrate (ice) formation under cryogenic conditions. Solid desiccant has typically been used for this purpose.

The feed stream 31 is cooled in heat exchanger 10 by heat exchange with cool residue gas (stream 39a), demethanizer reboiler liquids at 44° F. [7° C.] (stream 41), and demethanizer side reboiler liquids at −49° F. [−45° C.] (stream 40). (In some cases, the use of one or more supplemental external refrigeration streams may be advantageous as shown by the dashed line.) Stream 31a then enters separator 11 at −24° F. [−31° C.] and 900 psia [6,203 kPa(a)] where the vapor (stream 32) is separated from the condensed liquid (stream 33).

The vapor (stream 32) from separator 11 is divided into two streams, 34 and 37. The liquid (stream 33) from separator 11 is optionally divided into two streams, 35 and 38. (Stream 35 may contain from 0% to 100% of the separator liquid in stream 33. If stream 35 contains any portion of the separator liquid, then the process of FIG. 1 is according to U.S. Pat. No. 4,157,904. Otherwise, the process of FIG. 1 is according to U.S. Pat. No. 4,278,457.) For the process illustrated in FIG. 1, stream 35 contains 100% of the total separator liquid. Stream 34, containing about 31% of the total separator vapor, is combined with stream 35 and the combined stream 36 passes through heat exchanger 12 in heat exchange relation with the cold residue gas (stream 39) where it is cooled to substantial condensation. The resulting substantially condensed stream 36a at −134° F. [−92° C.] is then flash expanded through expansion valve 13 to the operating pressure (approximately 395 psia [2,721 kPa(a)]) of fractionation tower 17. During expansion a portion of the stream is vaporized, resulting in cooling of the total stream. In the process illustrated in FIG. 1, the expanded stream 36b leaving expansion valve 13 reaches a temperature of −140° F. [−96° C.] and is supplied to separator section 17a in the upper region of fractionation tower 17. The liquids separated therein become the top feed to demethanizing section 17b.

The remaining 69% of the vapor from separator 11 (stream 37) enters a work expansion machine 14 in which mechanical energy is extracted from this portion of the high pressure feed. The machine 14 expands the vapor substantially isentropically to the tower operating pressure, with the work expansion cooling the expanded stream 37a to a temperature of approximately −95° F. [−70° C.]. The typical commercially available expanders are capable of recovering on the order of 80-85% of the work theoretically available in an ideal isentropic expansion. The work recovered is often used to drive a centrifugal compressor (such as item 15) that can be used to re-compress the residue gas (stream 39b), for example. The partially condensed expanded stream 37a is thereafter supplied as feed to fractionation tower 17 at an upper mid-column feed point. The remaining separator liquid in stream 38 (if any) is expanded to the operating pressure of fractionation tower 17 by expansion valve 16, cooling stream 38a before it is supplied to fractionation tower 17 at a lower mid-column feed point.

The demethanizer in tower 17 is a conventional distillation column containing a plurality of vertically spaced trays, one or more packed beds, or some combination of trays and packing. As is often the case in natural gas processing plants, the fractionation tower may consist of two sections. The upper section 17a is a separator wherein the partially vaporized top feed is divided into its respective vapor and liquid portions, and wherein the vapor rising from the lower distillation or demethanizing section 17b is combined with the vapor portion of the top feed to form the cold demethanizer overhead vapor (stream 39) which exits the top of the tower. The lower, demethanizing section 17b contains the trays and/or packing and provides the necessary contact between the liquids falling downward and the vapors rising upward. The demethanizing section 17b also includes reboilers (such as the reboiler and the side reboiler described previously and supplemental reboiler 18) which heat and vaporize a portion of the liquids flowing down the column to provide the stripping vapors which flow up the column to strip the liquid product, stream 42, of methane and lighter components.

The liquid product stream 42 exits the bottom of the tower at 67° F. [19° C.], based on a typical specification of a methane to ethane ratio of 0.010:1 on a molar basis in the bottom product. The residue gas (demethanizer overhead vapor stream 39) passes countercurrently to the incoming feed gas in heat exchanger 12 where it is heated from −139° F. [−95° C.] to −37° F. [−38° C.] (stream 39a) and in heat exchanger 10 where it is heated to 91° F. [33° C.] (stream 39b). The residue gas is then re-compressed in two stages. The first stage is compressor 15 driven by expansion machine 14. The second stage is compressor 19 driven by a supplemental power source which compresses the residue gas (stream 39d) to sales line pressure. After cooling to 110° F. [43° C.] in discharge cooler 20, the residue gas product (stream 39e) flows to the sales gas pipeline at 915 psia [6,307 kPa(a)], sufficient to meet line requirements (usually on the order of the inlet pressure).

A summary of stream flow rates and energy consumption for the process illustrated in FIG. 1 is set forth in the following table:

TABLE I (FIG. 1)
Stream Flow Summary - Lb. Moles/Hr [kg moles/Hr]

| Stream | Methane | Ethane | Propane | Butanes+ | Total |
|---|---|---|---|---|---|
| 31 | 12,398 | 546 | 233 | 229 | 13,726 |
| 32 | 12,202 | 504 | 183 | 82 | 13,281 |
| 33 | 196 | 42 | 50 | 147 | 445 |
| 34 | 3,909 | 161 | 59 | 26 | 4,255 |
| 36 | 4,105 | 203 | 109 | 173 | 4,700 |
| 37 | 8,293 | 343 | 124 | 56 | 9,026 |
| 39 | 12,393 | 55 | 5 | 1 | 12,636 |
| 42 | 5 | 491 | 228 | 228 | 1,090 |

Recoveries*

| | |
|---|---|
| Ethane | 89.85% |
| Propane | 98.05% |
| Butanes+ | 99.71% |

Power

| | | |
|---|---|---|
| Residue Gas Compression | 5,569 HP | [9,155 kW] |

*(Based on un-rounded flow rates)

FIG. 2 is a process flow diagram showing one manner in which the design of the processing plant in FIG. 1 can be adjusted to operate at a lower $C_2$ component recovery level. This is a common requirement when the relative values of natural gas and liquid hydrocarbons are variable, causing recovery of the $C_2$ components to be unprofitable at times. The process of FIG. 2 has been applied to the same feed gas composition and conditions as described previously for FIG. 1. However, in the simulation of the process of FIG. 2, the process operating conditions have been adjusted to reject nearly all of $C_2$ components to the residue gas rather than recovering them in the bottom liquid product from the fractionation tower.

In this simulation of the process, inlet gas enters the plant at 100° F. [38° C.] and 915 psia [6,307 kPa(a)] as stream 31 and is cooled in heat exchanger 10 by heat exchange with cool residue gas stream 39a. (One consequence of operating the FIG. 2 process to reject nearly all of the $C_2$ components to the residue gas is that the temperatures of the liquids flowing down fractionation tower 17 are much warmer, to the point that side reboiler stream 40 and reboiler stream 41 can no longer be used to cool the inlet gas and all of the column reboil heat must be supplied by supplemental reboiler 18.) Cooled stream 31a enters separator 11 at 2° F. [−17° C.] and 900 psia [6,203 kPa(a)] where the vapor (stream 32) is separated from the condensed liquid (stream 33).

The vapor (stream 32) from separator 11 is divided into two streams, 34 and 37, and the liquid (stream 33) is optionally divided into two streams, 35 and 38. For the process illustrated in FIG. 2, stream 35 contains 100% of the total separator liquid. Stream 34, containing about 24% of the total separator vapor, is combined with stream 35 and the combined stream 36 passes through heat exchanger 12 in heat exchange relation with the cold residue gas (stream 39) where it is cooled to substantial condensation. The resulting substantially condensed stream 36a at −102° F. [−75° C.] is then flash expanded through expansion valve 13 to the operating pressure (approximately 398 psia [2,747 kPa(a)]) of fractionation tower 17. During expansion a portion of the stream is vaporized, resulting in cooling of the total stream. In the process illustrated in FIG. 2, the expanded stream 36b leaving expansion valve 13 reaches a temperature of −137° F. [−94° C.] and is supplied to fractionation tower 17 at the top feed point.

The remaining 76% of the vapor from separator 11 (stream 37) enters a work expansion machine 14 in which mechanical energy is extracted from this portion of the high pressure feed. The machine 14 expands the vapor substantially isentropically to the tower operating pressure, with the work expansion cooling the expanded stream 37a to a temperature of approximately −71° F. [−57° C.] before it is supplied as feed to fractionation tower 17 at an upper mid-column feed point. The remaining separator liquid in stream 38 (if any) is expanded to the operating pressure of fractionation tower 17 by expansion valve 16, cooling stream 38a before it is supplied to fractionation tower 17 at a lower mid-column feed point.

Note that when fractionation tower 17 is operated to reject the $C_2$ components to the residue gas product as shown in FIG. 2, the column is typically referred to as a deethanizer and its lower section 17b is called a deethanizing section. The liquid product stream 42 exits the bottom of deethanizer 17 at 230° F. [110° C.], based on a typical specification of an ethane to propane ratio of 0.020:1 on a molar basis in the bottom product. The residue gas (deethanizer overhead vapor stream 39) passes countercurrently to the incoming feed gas in heat exchanger 12 where it is heated from −108° F. [−78° C.] to −36° F. [−38° C.] (stream 39a) and in heat exchanger 10 where it is heated to 99° F. [37° C.] (stream 39b) as it provides cooling as previously described. The residue gas is then re-compressed in two stages, compressor 15 driven by expansion machine 14 and compressor 19 driven by a supplemental power source. After stream 39d is cooled to 110° F. [43° C.] in discharge cooler 20, the residue gas product (stream 39e) flows to the sales gas pipeline at 915 psia [6,307 kPa(a)].

A summary of stream flow rates and energy consumption for the process illustrated in FIG. 2 is set forth in the following table:

TABLE II (FIG. 2)
Stream Flow Summary - Lb. Moles/Hr [kg moles/Hr]

| Stream | Methane | Ethane | Propane | Butanes+ | Total |
|---|---|---|---|---|---|
| 31 | 12,398 | 546 | 233 | 229 | 13,726 |
| 32 | 12,304 | 526 | 208 | 117 | 13,470 |
| 35 | 94 | 20 | 25 | 112 | 256 |
| 34 | 3,040 | 130 | 51 | 29 | 3,328 |
| 36 | 3,134 | 150 | 76 | 141 | 3,584 |
| 37 | 9,264 | 396 | 157 | 88 | 10,142 |
| 59 | 12,398 | 542 | 15 | 2 | 13,276 |
| 42 | 0 | 4 | 218 | 227 | 450 |

Recoveries*

| | |
|---|---|
| Propane | 93.60% |
| Butanes+ | 99.12% |

Power

| | | |
|---|---|---|
| Residue Gas Compression | 5,565 HP | [9,149 kW] |

*(Based on un-rounded flow rates)

Product economics sometimes favor rejecting only a portion of the $C_2$ components to the residue gas product. FIG. 3 is a process flow diagram showing one manner in which the design of the processing plant in FIG. 1 can be adjusted to operate at an intermediate $C_2$ component recovery level. The process of FIG. 3 has been applied to the same feed gas composition and conditions as described previously for FIGS. 1 and 2. However, in the simulation of the process of FIG. 3, the process operating conditions have been adjusted to receiver about half as much of the $C_2$ components in the bottom liquid product from the fractionation tower compared to the quantity of $C_2$ components recovered by the FIG. 1 process.

In this simulation of the process, inlet gas enters the plant at 100° F. [38° C.] and 915 psia [6,307 kPa(a)] as stream 31 and is cooled in heat exchanger 10 by heat exchange with cool residue gas stream 39a and demethanizer side reboiler liquids at 63° F. [17° C.] (stream 40). (At the $C_2$ component recovery level of the FIG. 3 process, the side reboiler stream 40 is still cool enough to be used to cool the inlet gas, reducing the amount of column reboil heat that must be supplied by supplemental reboiler 18.) Cooled stream 31a enters separator 11 at 8° F. [−14° C.] and 900 psia [6,203 kPa(a)] where the vapor (stream 32) is separated from the condensed liquid (stream 33).

The vapor (stream 32) from separator 11 is divided into two streams, 34 and 37, and the liquid (stream 33) is optionally divided into two streams, 35 and 38. For the process illustrated in FIG. 3, stream 35 contains 100% of the total separator liquid. Stream 34, containing about 27% of the total separator vapor, is combined with stream 35 and the combined stream 36 passes through heat exchanger 12 in heat exchange relation with the cold residue gas (stream 39) where it is cooled to substantial condensation. The resulting substantially condensed stream 36a at −120° F. [−85° C.] is then flash expanded through expansion valve 13 to the operating pressure (approximately 384 psia [2,644 kPa(a)] of fractionation tower 17. During expansion a portion of the stream is vaporized, resulting in cooling of the total stream. In the process illustrated in FIG. 3, the expanded stream 36b leaving expansion valve 13 reaches a temperature of −141° F. [−96° C.] and is supplied to fractionation tower 17 at the top feed point.

The remaining 73% of the vapor from separator 11 (stream 37) enters a work expansion machine 14 in which mechanical energy is extracted from this portion of the high pressure feed. The machine 14 expands the vapor substantially isentropically to the tower operating pressure, with the work expansion cooling the expanded stream 37a to a temperature of approximately −69° F. [−56° C.] before it is supplied as feed to fractionation tower 17 at an upper mid-column feed point. The remaining separator liquid in stream 38 (if any) is expanded to the operating pressure of fractionation tower 17 by expansion valve 16, cooling stream 38a before it is supplied to fractionation tower 17 at a lower mid-column feed point.

The liquid product stream 42 exits the bottom of the tower at 130° F. [54° C.]. The residue gas (deethanizer overhead vapor stream 39) passes countercurrently to the incoming feed gas in heat exchanger 12 where it is heated from −122° F. [−86° C.] to −29° F. [−34° C.] (stream 39a) and in heat exchanger 10 where it is heated to 86° F. [130° C.] (stream 39b) as it provides cooling as previously described. The residue gas is then re-compressed in two stages, compressor 15 driven by expansion machine 14 and compressor 19 driven by a supplemental power source. After stream 39d is cooled to 110° F. [43° C.] in discharge cooler 20, the residue gas product (stream 39e) flows to the sales gas pipeline at 915 psia [6,307 kPa(a)].

A summary of stream flow rates and energy consumption for the process illustrated in FIG. 3 is set forth in the following table:

TABLE III (FIG. 3)
Stream Flow Summary - Lb. Moles/Hr [kg moles/Hr]

| Stream | Methane | Ethane | Propane | Butanes+ | Total |
|---|---|---|---|---|---|
| 31 | 12,398 | 546 | 233 | 229 | 13,726 |
| 32 | 12,316 | 529 | 211 | 124 | 13,496 |
| 33 | 82 | 17 | 22 | 105 | 230 |
| 34 | 3,351 | 144 | 57 | 34 | 3,671 |
| 36 | 3,433 | 161 | 79 | 139 | 3,901 |
| 37 | 8,965 | 385 | 154 | 90 | 9,825 |
| 39 | 12,398 | 300 | 8 | 1 | 13,025 |
| 42 | 0 | 246 | 225 | 228 | 701 |

Recoveries*

| | |
|---|---|
| Ethane | 45.00% |
| Propane | 96.51% |
| Butanes+ | 99.56% |

Power

| | | |
|---|---|---|
| Residue Gas Compression | 5,564 HP | [9,147 kW] |

*(Based on un-rounded flow rates)

DESCRIPTION OF THE INVENTION

Example 1

In those cases where the $C_2$ component recovery level in the liquid product must be reduced (as in the FIG. 2 prior art process described previously, for instance), the present invention offers significant efficiency advantages over the prior art process depicted in FIG. 2. FIG. 4 illustrates a flow diagram of the FIG. 2 prior art process that has been adapted to use the present invention. The operating conditions of the FIG. 4 process have been adjusted as shown to reduce the ethane content of the liquid product to the same level as that of the FIG. 2 prior art process. The feed gas composition and conditions considered in the process presented in FIG. 4 are the same as those in FIG. 2. Accordingly, the FIG. 4 process can be compared with that of the FIG. 2 process to illustrate the advantages of the present invention.

Most of the process conditions shown for the FIG. 4 process are much the same as the corresponding process conditions for the FIG. 3 process. The main differences are the disposition of flash expanded substantially condensed stream 36b and column overhead vapor stream 39. In the FIG. 4 process, substantially condensed stream 36a is flash expanded through expansion valve 13 to slightly above the operating pressure (approximately 402 psia [2,774 kPa(a)]) of fractionation tower 17. During expansion a portion of the stream may be vaporized, resulting in cooling of the total stream. In the process illustrated in FIG. 4, the expanded stream 36b leaving expansion valve 13 reaches a temperature of −138° F. [−94° C.] before it is directed into a heat and mass transfer means inside rectifying section 117a of processing assembly 117. This heat and mass transfer means may be comprised of a fin and tube type heat exchanger, a plate type heat exchanger, a brazed aluminum type heat exchanger, or other type of heat transfer device, including multi-pass and/or multi-service heat exchangers. The heat and mass transfer means is configured to provide heat exchange between a combined vapor stream flowing upward through one pass of the heat and mass transfer means, and the flash expanded substantially condensed stream 36b flowing downward, so that the combined vapor stream is cooled while heating the expanded stream. As the combined vapor stream is cooled, a portion of it is condensed and falls downward while the remaining combined vapor stream continues flowing upward through the heat and mass transfer means. The heat and mass transfer means provides continuous contact between the condensed liquid and the combined vapor stream so that it also functions to provide mass transfer between the vapor and liquid phases, thereby providing rectification of the combined vapor stream. The condensed liquid from the bottom of the heat and mass transfer means is directed to separator section 117*b* of processing assembly 117.

The flash expanded stream 36*b* is further vaporized as it provides cooling and partial condensation of the combined vapor stream, and exits the heat and mass transfer means in rectifying section 117*a* at 105° F. [−76° C.]. The heated flash expanded stream discharges into separator section 117*b* of processing assembly 117 and is separated into its respective vapor and liquid phases The vapor phase combines with overhead vapor stream 39 to form the combined vapor stream that enters the heat and mass transfer means in rectifying section 117*a* as previously described, and the liquid phase combines with the condensed liquid from the bottom of the heat and mass transfer means to form combined liquid stream 152. Combined liquid stream 152 leaves the bottom of processing assembly 117 and is pumped to higher pressure by pump 21 so that stream 152*a* at −102° F. [−75° C.] can enter fractionation column 17 at the top feed point. The vapor remaining from the cooled combined vapor stream leaves the heat and mass transfer means inside rectifying section 117*a* of processing assembly 117 at −117° F. [−83° C.] as cold residue gas stream 151, which is then heated and compressed as described previously for stream 39 in the FIG. 2 process.

A summary of stream flow rates and energy consumption for the process illustrated in FIG. 4 is set forth in the following table:

TABLE IV (FIG. 4)
Stream Flow Summary - Lb. Moles/Hr [kg moles/Hr]

| Stream | Methane | Ethane | Propane | Butanes+ | Total |
|---|---|---|---|---|---|
| 31 | 12,398 | 546 | 233 | 229 | 13,726 |
| 32 | 12,318 | 529 | 212 | 125 | 13,499 |
| 33 | 80 | 17 | 21 | 104 | 227 |
| 34 | 3,570 | 153 | 61 | 36 | 3,912 |
| 36 | 3,650 | 170 | 82 | 140 | 4,139 |
| 37 | 8,748 | 376 | 151 | 89 | 9,587 |
| 39 | 9,525 | 856 | 31 | 4 | 10,699 |
| 152 | 777 | 485 | 112 | 144 | 1,578 |
| 151 | 12,398 | 541 | 1 | 0 | 13,260 |
| 42 | 0 | 5 | 232 | 229 | 466 |

Recoveries*

| | |
|---|---|
| Propane | 99.65% |
| Butanes+ | 100.00% |

Power

| | | |
|---|---|---|
| Residue Gas Compression | 5,565 HP | [9,149 kW] |

*(Based on un-rounded flow rates)

A comparison of Tables II and IV shows that, compared to the prior art, the present invention improves propane recovery from 93.60% to 99.65% and butane+ recovery from 99.12% to 100.00%. The economic impact or these improved recoveries is significant. Using an average incremental value $ 1.08/gallon [€ 214/m³] for hydrocarbon liquids compared to the corresponding hydrocarbon gases, the improved recoveries represent more than US$ 1,120,000 [€ 835,000] of additional annual revenue for the plant operator. Comparison of Tables II and IV further shows that these increased product yields were achieved using the same power as the prior art. In terms of the recovery efficiency (defined by the quantity of $C_3$ components and heavier components recovered per unit of power), the present invention represents more than a 3% improvement over the prior art of the FIG. 2 process.

The improvement in recovery efficiency provided by the present invention over that of the prior art of the FIG. 2 process is primarily due to the indirect cooling of the column vapor provided by flash expanded stream 36*b* in rectifying section 117*a* of processing assembly 117, rather than the direct-contact cooling that characterizes stream 36*b* in the prior art process of FIG 2. Although stream 36*b* is quite cold, it is not an ideal reflux stream because it contains significant concentrations of the $C_3$ components and $C_4+$ components that deethanizer 17 is supposed to capture, resulting in losses of these desirable components due to equilibrium effects at the top of column 17 for the prior art process of FIG. 2. For the present invention shown in FIG. 4, however, there are no equilibrium effects to overcome because there is no direct contact between flash expanded stream 36*b* and the combined vapor stream to be rectified.

The present invention has the further advantage of using the heat and mass transfer means in rectifying section 117*a* to simultaneously cool the combined vapor steam and condense the heavier hydrocarbon components from it, providing more efficient rectification than using reflux in a conventional distillation column. As a result, more of the $C_3$ components and heavier hydrocarbon components can be removed from the combined vapor stream using the refrigeration available in expanded stream 36*b* than is possible using conventional mass transfer equipment and conventional heat transfer equipment.

The present invention offers two other advantages over the prior art in addition to the increase in processing efficiency. First, the compact arrangement of processing assembly 117 of the present invention replaces three separate equipment items in the prior art of U.S. Pat. No. 4,854,955 (heat exchanger 23, the upper absorbing section in the top of distillation column 24, and reflux drum 26 in FIG. 4 of U.S. Pat. No. 4,854,955) with a single equipment item (processing assembly 117 in FIG. 4 of the present invention). This reduces the plot space requirements and eliminates the interconnecting piping, reducing the capital cost of modifying a process plant to use the present invention. Second, elimination of the interconnecting piping means that a processing plant modified to use the present invention has far fewer flanged connections compared to the prior art of U.S. Pat. No. 4,854,955, reducing the number of potential leak sources in the plant. Hydrocarbons are volatile organic compounds (VOCs), some of which are classified as greenhouse gases and some of which may be precursors to atmospheric ozone formation, which means the present invention reduces the potential for atmospheric releases that may damage the environment.

One additional advantage of the present invention is how easily it can be incorporated into an existing gas processing plant to effect the superior performance described above. As shown in FIG. 4, only two connections (commonly referred to as "tie-ins") to the existing plant are needed: for flash expanded substantially condensed stream 36*b* (represented by the dashed line between stream 36*b* and stream 152*a* that is removed from service), and for column overhead vapor stream 39 (represented by the dashed line between stream 39 and stream 151 that is removed from service). The existing plant can continue to operate while the new processing assembly 117 is installed near fractionation tower 17, with just a short plant shutdown when installation is complete to make the new tie-ins to these two existing lines. The plant can then be restarted, with all of the existing equipment remaining in service and operating exactly as before, except that the product recovery is now higher with no increase in residue gas compression power.

Example 2

The present invention also offers advantages when product economics favor rejecting only a portion of the $C_2$ components to the residue gas product. The operating conditions of the FIG. 4 process can be altered as illustrated in FIG. 5 to increase the ethane content of the liquid product to the same level as that of the FIG. 3 prior art process. The feed gas composition and conditions considered in the process presented in FIG. 5 are the same as those in FIG. 3. Accordingly, the FIG. 5 process can be compared with that of the FIG. 3 process to further illustrate the advantages of the present invention.

Most of the process conditions shown for the FIG. 5 process are much the same as the corresponding process conditions for the FIG. 3 process. The main differences are again the disposition of flash expanded substantially condensed stream 36b and column overhead vapor stream 39. In the FIG. 5 process, substantially condensed stream 36a is flash expanded through expansion valve 13 to slightly above the operating pressure (approximately 390 psia [2,691 kPa (a)]) of fractionation tower 17. During expansion a portion of the stream may be vaporized, resulting in cooling of the total stream. In the process illustrated in FIG. 5, the expanded stream 36b leaving expansion valve 13 reaches a temperature of −141° F. [−96° C.] before it is directed into the heat and mass transfer means inside rectifying section 117a of processing assembly 117. As the combined vapor stream flows upward through one pass of the heat and mass transfer means and is cooled, a portion of it is condensed and falls downward while the remaining combined vapor stream continues flowing upward. The heat and mass transfer means provides continuous contact between the condensed liquid and the combined vapor stream so that it also functions to provide mass transfer between the vapor and liquid phases, thereby providing rectification of the combined vapor stream. The condensed liquid from the bottom of the heat and mass transfer means is directed to separator section 117b of processing assembly 117.

The flash expanded stream 36b is further vaporized as it provides cooling and partial condensation of the combined vapor stream, and exits the heat and mass transfer means in rectifying section 117a at −136° F. [−93° C.]. The heated flash expanded stream discharges into separator section 117b of processing assembly 117 and is separated into its respective vapor and liquid phases. The vapor phase combines with overhead vapor stream 39 to form the combined vapor stream that enters the heat and mass transfer means in rectifying section 117a as previously described, and the liquid phase combines with the condensed liquid from the bottom of the heat and mass transfer means to form combined liquid stream 152. Combined liquid stream 152 leaves the bottom of processing assembly 117 and is pumped to higher pressure by pump 21 so that stream 152a at −133° F. [−92° C.] can enter fractionation column 17 at the top feed point. The vapor remaining from the cooled combined vapor stream leaves the heat and mass transfer means inside rectifying section 117a of processing assembly 117 at −128° F. [−89° C.] as cold residue gas stream 151, which is then heated and compressed as described previously for stream 39 in the FIG. 3 process.

A summary of stream flow rates and energy consumption for the process illustrated in FIG. 5 is set forth in the following table:

TABLE V (FIG. 5)
Stream Flow Summary - Lb. Moles/Hr [kg moles/Hr]

| Stream | Methane | Ethane | Propane | Butanes+ | Total |
|---|---|---|---|---|---|
| 31 | 12,398 | 546 | 233 | 229 | 13,726 |
| 32 | 12,317 | 529 | 212 | 124 | 13,497 |
| 33 | 81 | 17 | 21 | 105 | 229 |
| 34 | 3,632 | 156 | 63 | 37 | 3,980 |
| 36 | 3,713 | 173 | 84 | 142 | 4,209 |
| 37 | 8,685 | 373 | 149 | 87 | 9,517 |
| 39 | 10,689 | 425 | 12 | 1 | 11,435 |
| 152 | 2,004 | 298 | 95 | 143 | 2,627 |
| 151 | 12,398 | 300 | 1 | 0 | 13,017 |
| 42 | 0 | 246 | 232 | 229 | 709 |

Recoveries*

| | |
|---|---|
| Ethane | 45.00% |
| Propane | 99.65% |
| Butanes+ | 100.00% |

Power

| | | |
|---|---|---|
| Residue Gas Compression | 5,565 HP | [9,149 kW] |

*(Based on un-rounded flow rates)

A comparison of Tables III and V shows that, compared to the prior art, the present invention improves propane recovery from 96.51% to 99.65% and butane+ recovery from 99.56% to 100.00%. The economic impact of these improved recoveries is significant. Using an average incremental value $0.74/gallon [€ 145/m$^3$] for hydrocarbon liquids compared to the corresponding hydrocarbon gases, the improved recoveries represent more than US$ 575,000 [€ 430,000] of additional annual revenue for the plant operator. Comparison of Tables III and V further shows that these increased product yields were achieved using the same power as the prior art. In terms of the recovery efficiency (defined by the quantity of $C_3$ components and heavier components recovered per unit of power), the present invention represents nearly a 2% improvement over the prior art of the FIG. 3 process.

The FIG. 5 embodiment of the present invention provides the same advantages related to processing efficiency and the compact arrangement of processing assembly 117 as the FIG. 4 embodiment. The FIG. 5 embodiment of the present invention overcomes the equilibrium limitations associated with expanded stream 36b in the prior art FIG. 3 process to remove the heavier components from the column overhead vapor via indirect cooling and simultaneous mass transfer in rectifying section 117a of process assembly 117. The FIG. 5 embodiment of the present invention also replaces the three separate equipment items in the prior art of the U.S. Pat. No. 4,854,955 process with a single equipment item (processing assembly 117 in FIG. 5). This reduces the plot space requirements and eliminates the interconnecting piping, reducing the capital cost to modify an existing process plant to use this embodiment of the present invention while also reducing the potential for atmospheric releases of hydrocarbons that may damage the environment.

Example 3

The present invention can also be operated to recover the maximum amount of $C_2$ components in the liquid product. The operating conditions of the FIG. 4 process can be altered as illustrated in FIG. 6 to increase the ethane content of the liquid product to the same level as that of the FIG. 1 prior art process. The feed gas composition and conditions considered in the process presented in FIG. 6 are the same as those in FIG. 1. Accordingly, the FIG. 6 process can be compared with that of the FIG. 1.

Most of the process conditions shown for the FIG. 6 process are much the same as the corresponding process conditions for the FIG. 1 process. The main differences are again the disposition of flash expanded substantially condensed stream 36*b* and column overhead vapor stream 39. In the FIG. 6 process, substantially condensed stream 36*a* is flash expanded through expansion valve 13 to slightly above the operating pressure (approximately 396 psia [2,731 kPa (a)]) of fractionation tower 17. During expansion a portion of the stream may be vaporized, resulting in cooling of the total stream. In the process illustrated in FIG. 6, the expanded stream 36*b* leaving expansion valve 13 reaches a temperature of −140° F. [−96° C.] before it is directed into the heat and mass transfer means inside rectifying section 117*a* of processing assembly 117. As the combined vapor stream flows upward through one pass of the heat and mass transfer means and is cooled, a portion of it is condensed and falls downward while the remaining combined vapor stream continues flowing upward. The heat and mass transfer means provides continuous contact between the condensed liquid and the combined vapor stream so that it also functions to provide mass transfer between the vapor and liquid phases, thereby providing rectification of the combined vapor stream. The condensed liquid from the bottom of the heat and mass transfer means is directed to separator section 117*b* of processing assembly 117.

The flash expanded stream 36*b* is further vaporized as it provides cooling and partial condensation of the combined vapor stream, and exits the heat and mass transfer means in rectifying section 117*a* at −141° F. [−96° C.]. (Note that the temperature of stream 36*b* drops slightly as it is heated, due to the pressure drop through the heat and mass transfer means and the resulting vaporization of some of the liquid methane contained in the stream.) The heated flash expanded stream discharges into separator section 117*b* of processing assembly 117 and is separated into its respective vapor and liquid phases. The vapor phase combines with overhead vapor stream 39 to form the combined vapor stream that enters the heat and mass transfer means in rectifying section 117*a* as previously described, and the liquid phase combines with the condensed liquid from the bottom of the heat and mass transfer means to form combined liquid stream 152. Combined liquid stream 152 leaves the bottom of processing assembly 117 and is pumped to higher pressure by pump 21 so that stream 152*a* at −141° F. [−96° C.] can enter fractionation column 17 at the top feed point. The vapor remaining from the cooled combined vapor stream leaves the heat and mass transfer means inside rectifying section 117*a* of processing assembly 117 at −139° F. [−95° C.] as cold residue gas stream 151, which is then heated and compressed as described previously for stream 39 in the FIG. 1 process.

A summary of stream flow rates and energy consumption for the process illustrated in FIG. 6 is set forth in the following table:

TABLE VI (FIG. 6)
Stream Flow Summary - Lb. Moles/Hr [kg moles/Hr]

| Stream | Methane | Ethane | Propane | Butanes+ | Total |
|---|---|---|---|---|---|
| 31 | 12,398 | 546 | 233 | 229 | 13,726 |
| 32 | 12,200 | 503 | 183 | 82 | 13,278 |
| 33 | 198 | 43 | 50 | 147 | 448 |
| 34 | 3,784 | 156 | 57 | 25 | 4,118 |
| 36 | 3,982 | 199 | 107 | 172 | 4,566 |
| 37 | 8,416 | 347 | 126 | 57 | 9,160 |
| 39 | 12,265 | 55 | 5 | 1 | 12,508 |
| 152 | 3,854 | 198 | 107 | 172 | 4,432 |
| 151 | 12,393 | 56 | 5 | 1 | 12,642 |
| 42 | 5 | 490 | 228 | 228 | 1,084 |

| Recoveries* | |
|---|---|
| Ethane | 89.79% |
| Propane | 98.03% |
| Butanes+ | 99.71% |

| Power | | |
|---|---|---|
| Residue Gas Compression | 5,569 HP | [9,155 kW] |

*(Based on un-rounded flow rates)

A comparison of Tables I and VI shows that the present invention achieves essentially the same recovery levels as the prior art when the process is operated to recover the maximum amount of $C_2$ components. When operated in this manner, the temperature driving force for indirect cooling and simultaneous mass transfer in rectifying section 117*a* of process assembly 117 is very low because the temperature of column overhead stream 39 is almost the same as the temperature of flash expanded stream 36*b*, reducing the effectiveness of rectifying section 117*a*. Although there is no improvement in the component recoveries compared to the prior art when the present invention is operated in this manner, there is no decline either. This means there is no penalty when economies favor operating the plant to recover the maximum amount of $C_2$ components in the liquid product, but the plant has all the advantages described previously for Examples 1 and 2 when economics favor operating the plant to reject some or all of the $C_2$ components to the residue gas product.

Other Embodiments

Some circumstances may favor also mounting the liquid pump inside the processing assembly to further reduce the number of equipment items and the plot space requirements. Such an embodiment is shown in FIG. 7, with pump 121 mounted inside processing assembly 117 as shown to send the combined liquid stream from separator section 117*b* to the top feed point of column 17 via conduit 152. The pump and its driver may both be mounted inside the processing assembly if a submerged pump or canned motor pump is used, or just the pump itself may be mounted inside the processing assembly (using a magnetically-coupled drive for the pump, for instance). For either option, the potential for atmospheric releases of hydrocarbons that may damage the environment is reduced still further.

Some circumstances may favor locating the processing assembly at a higher elevation than the top feed point on fractionation column 17. In such cases, it may be possible for combined liquid stream 152 to flow to the top feed point on fractionation column 17 by gravity head as shown in FIG. 8, eliminating the need for pump 21/121 shown in the FIGS. 4 through 7 embodiments.

The present invention provides improved recovery of $C_3$ components and heavier hydrocarbon components per amount of utility consumption required to operate the process. An improvement in utility consumption required for operating the process may appear in the form of reduced power requirements for compression or re-compression, reduced power requirements tor external refrigeration, reduced energy requirements for supplemental heating, or a combination thereof.

While there have been described what are believed to be preferred embodiments of the invention, those skilled in the art will recognize that other and further modifications may be made thereto, e.g. to adapt the invention to various conditions, types of feed, or other requirements without departing from the spirit of the present invention as defined by the following claims.

We claim:

1. In a process for the separation of a gas stream containing methane, $C_2$ components, $C_3$ components, and heavier hydrocarbon components into a volatile residue gas fraction and a relatively less volatile fraction containing a major portion of said $C_2$ components, $C_3$ components, and heavier hydrocarbon components or said $C_3$ components and heavier hydrocarbon components, in which process (a) said gas stream is treated in one or more heat exchange steps and at least one division step to produce at least a first stream that has been cooled under pressure to condense substantially all of it, and at least a second stream that has been cooled under pressure;

(b) said substantially condensed first stream is expanded to a lower pressure whereby it is further cooled, and thereafter supplied at a top feed position on a distillation column that produces at least an overhead vapor stream and a bottom liquid stream;

(c) said cooled second stream is expanded to said lower pressure, and thereafter supplied to said distillation column at a mid-column feed position; and (d) at least said expanded further cooled first stream and said expanded second stream are fractionated in said distillation column at said lower pressure whereby the components of said relatively less volatile fraction are recovered in said bottom liquid stream and said volatile residue gas fraction is discharged as said overhead vapor stream;

the improvement wherein (1) said expanded further cooled first stream is heated in a heat and mass transfer means housed in a processing assembly and thereafter discharged as a vapor fraction and a liquid fraction;

(2) said overhead vapor stream is combined with said vapor fraction to form a combined vapor stream;

(3) said combined vapor stream is cooled in said heat and mass transfer means, thereby to supply at least a portion of the heating of step (1) while simultaneously condensing the less volatile components from said combined vapor stream, thereby forming a condensed stream and a residual vapor stream, and thereafter discharging said residual vapor stream from said processing assembly as said volatile residue gas fraction;

(4) said condensed stream is combined with said liquid fraction to form a combined liquid stream;

(5) said combined liquid stream is supplied to said top feed position of said distillation column; and (6) the quantity and temperature of said combined liquid stream to said distillation column are effective to maintain the overhead temperature of said distillation column at a temperature whereby the major portions of the components in said relatively less volatile fraction are recovered in said bottom liquid stream.

2. The process according to claim 1 wherein said combined liquid stream is supplied to said top feed position of said distillation column using a pumping means.

3. The process according to claim 2 wherein said pumping means is housed in said processing assembly.

4. The process according to claim 1, 2, or 3 wherein (1) said gas stream is cooled under pressure in said one or more heat exchange steps sufficiently to partially condense it;

(2) said partially condensed gas stream is separated thereby to provide a vapor stream and at least one liquid stream;

(3) said vapor stream is divided in said at least one division step to produce at least a first vapor stream and a second vapor stream;

(4) said first vapor stream is cooled under pressure in said one or more heat exchange steps to condense substantially all of it and thereby form said substantially condensed first stream;

(5) said second vapor stream is expanded to said lower pressure, thereby forming said expanded second stream;

(6) at least a portion of said at least one liquid stream is expanded to said lower pressure, whereupon said expanded liquid stream is supplied to said distillation column at a lower mid-column feed position below said mid-column feed position; and (7) at least said expanded further cooled first stream, said expanded second stream, and said expanded liquid stream are fractionated in said distillation column at said lower pressure whereby the components of said relatively less volatile fraction are recovered in said bottom liquid stream.

5. The process according to claim 4 wherein (1) said first vapor stream is combined with at least a portion of said at least one liquid stream to form a combined stream, whereupon said combined stream is cooled under pressure in said one or more heat exchange steps to condense substantially all of it and is thereafter expanded to said lower pressure whereby it is further cooled;

(2) said expanded cooled combined stream is heated in said heat and mass transfer means and thereafter discharged as said vapor fraction and said liquid fraction; and (3) any remaining portion of said at least one liquid stream is expanded to said lower pressure, whereupon said expanded liquid stream is supplied to said distillation column at said lower mid-column feed position.

* * * * *

UNITED STATES PATENT AND TRADEMARK OFFICE
CERTIFICATE OF CORRECTION

PATENT NO. : 9,637,428 B2
APPLICATION NO. : 14/462056
DATED : May 2, 2017
INVENTOR(S) : Hank M. Hudson et al.

It is certified that error appears in the above-identified patent and that said Letters Patent is hereby corrected as shown below:

In the Specification

Column 1:
Line 36, "incremented" should read --incremental--.

Column 9:
Line 1, "receiver" should read --recover--; and
Line 56, "[130°C.]" should read --[30°C.]--.

Column 11:
Line 65, "or" should read --of--.

Signed and Sealed this
Twelfth Day of September, 2017

Joseph Matal
*Performing the Functions and Duties of the*
*Under Secretary of Commerce for Intellectual Property and*
*Director of the United States Patent and Trademark Office*